United States Patent

Chen et al.

[11] Patent Number: 5,998,620
[45] Date of Patent: Dec. 7, 1999

[54] SYNTHESIS OF INTERMEDIATES USEFUL IN PREPARING TRICYCLIC COMPOUNDS

[75] Inventors: Xing Chen, Plainsboro; Marc Poirier, Parlin; Yee-Shing Wong, Florham Park; Guang-Zhong Wu, Neshanic Station, all of N.J.

[73] Assignee: Schering Corporation, Kenilworth, N.J.

[21] Appl. No.: 09/045,803

[22] Filed: Mar. 23, 1998

Related U.S. Application Data

[60] Provisional application No. 60/042,068, Mar. 25, 1997.

[51] Int. Cl.[6] .................................................. C07D 221/06
[52] U.S. Cl. ................................................................ 546/93
[58] Field of Search ................................................. 546/93

[56] References Cited

U.S. PATENT DOCUMENTS

| | | | |
|---|---|---|---|
| 4,282,233 | 8/1981 | Villani et al. | 424/267 |
| 4,659,716 | 4/1987 | Villani et al. | 546/93 |
| 4,731,447 | 3/1988 | Schumacher et al. | 546/93 |
| 5,151,423 | 9/1992 | Piwinski et al. | 514/254 |
| 5,162,335 | 11/1992 | Vandewalle et al. | 546/93 |
| 5,760,232 | 6/1998 | Chen et al. | 546/93 |

FOREIGN PATENT DOCUMENTS

| | | |
|---|---|---|
| 0 011 858 | 6/1980 | European Pat. Off. . |
| 0 396 083 | 11/1990 | European Pat. Off. . |
| 2 094 790 | 9/1982 | United Kingdom . |
| WO 96/31478 | 10/1996 | WIPO . |
| WO 97/23478 | 7/1997 | WIPO . |

OTHER PUBLICATIONS

Basha et al, *Tet. Lett.*, 48 (1977), pp. 4171–4174.

*Primary Examiner*—John Kight
*Assistant Examiner*—Raymond Covington
*Attorney, Agent, or Firm*—Anita W. Magatti

[57] ABSTRACT

The invention relates to a process for preparing a compound of the formula

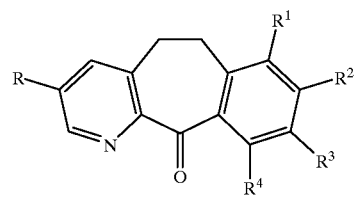

comprising reacting a bromo-substituted pyridine with an amine of the formula $NHR^5R^6$, reacting the resulting amide with an iodo-halomethyl-substituted compound and cyclizing the resultant product, wherein R, $R^1$, $R^2$, $R^3$ and $R^4$ are as defined in the specification; also claimed are a compound of the formula

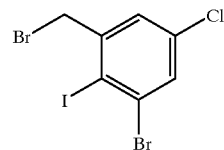

and a process for preparing it from the corresponding halo-substituted benzoic acid.

26 Claims, No Drawings

SYNTHESIS OF INTERMEDIATES USEFUL IN PREPARING TRICYCLIC COMPOUNDS

This application claims benefit of Provisional application No. 60/042,068 filed Mar. 25, 1997.

BACKGROUND OF THE INVENTION

This invention provides an improved process for preparing intermediates useful in the preparation of tricyclic compounds known as antihistamines and as inhibitors of farnesyl protein transferase (FPT). In particular, the compounds of this invention are useful in the preparation of antihistamines such as those disclosed in U.S. Pat. Nos. 4,282,233 and 5,151,423, and of FPT inhibitors disclosed in International Application No. PCT/US96/19603, filed Dec. 19, 1996.

SUMMARY OF THE INVENTION

This invention provides a process for preparing a compound of the formula

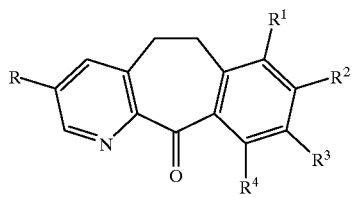

I wherein:
R, $R^1$, $R^2$, $R^3$ and $R^4$ are independently selected from the group consisting of hydrogen and halo; comprising:
(a) reacting a compound of formula 1

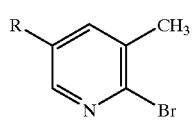

1

(i) with an amine of the formula $NHR^5R^6$, wherein $R^5$ is hydrogen and $R^6$ is $C_1$–$C_6$ alkyl, aryl or heteroaryl; $R^5$ is $C_1$–$C_6$ alkyl, aryl or heteroaryl and $R^6$ is hydrogen; $R^5$ and $R^6$ are independently selected from the group consisting of $C_1$–$C_6$ alkyl and aryl; or $R^5$ and $R^6$, together with the nitrogen to which they are attached, form a ring comprising 4 to 6 carbon atoms or comprising 3 to 5 carbon atoms and one hetero moiety selected from the group consisting of —O— and —$NR^9$—, wherein $R^9$ is H, $C_1$–$C_6$ alkyl or phenyl; in the presence of a palladium catalyst and carbon monoxide to obtain an amide of formula 2:

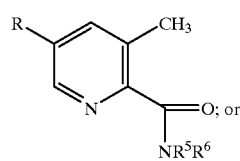

2

(ii) with an alcohol of the formula $R^{10}OH$, wherein $R^{10}$ is $C_1$–$C_6$ lower alkyl or $C_3$–$C_6$ cycloalkyl, in the presence of a palladium catalyst and carbon monoxide to obtain the ester of formula 2A

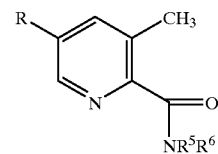

2A followed by reacting the compound of 2A with an amine of formula $NHR^5R^6$ to obtain the amide of formula 2;
(b) reacting the amide of formula 2 with an iodo-substituted compound of formula 3

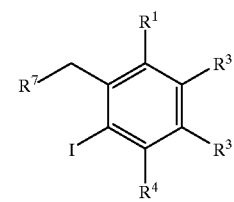

3 wherein $R^1$, $R^2$, $R^3$ and $R^4$ are as defined above and $R^7$ is Cl or Br, in the presence of a strong base to obtain a compound of formula 4

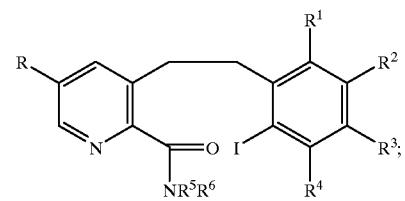

4

(c) cyclizing a compound of formula 4 with a reagent of the formula $R^8MgL$, or when none of R, $R^1$, $R^2$, $R^3$ and $R^4$ are bromo, with a reagent of the formula $R^8Li$, wherein $R^8$ is $C_1$–$C_8$ alkyl, aryl or heteroaryl and L is Br or Cl; provided that prior to cyclization, compounds wherein $R^5$ or $R^6$ is hydrogen are reacted with a suitable N-protecting group.

This invention also claims the intermediate compound of formula 3, in particular a compound of formula 3 wherein $R^1$ and $R^3$ are hydrogen, $R^2$ is chloro, and each of $R^4$ and $R^7$ are bromo, i.e., a compound of formula 5:

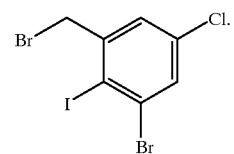

5

This invention also claims the intermediate compound of formula 4, in particular a compound of formula 4 wherein $R^1$ and $R^3$ are hydrogen, $R^2$ is chloro, and each of R and $R^4$ are bromo, i.e., a compound of formula 4A, or wherein $R^1$, $R^2$, $R^3$ and $R^4$ are hydrogen and $R^2$ is chloro, i.e., a compound of formula 4B:

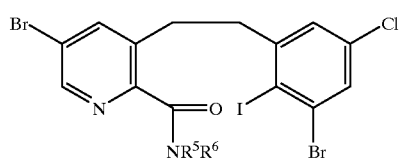

4A

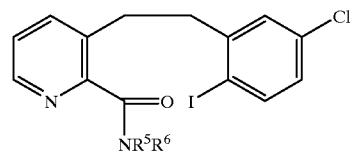

4B

Also claimed herein is a process for preparing a compound of formula 5 comprising:

i) brominating 2-amino chlorobenzoic acid of formula 6

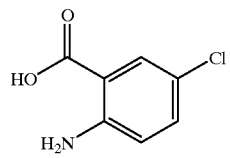

6 to obtain 2-amino-3-bromo-5-chlorobenzoic acid of formula 7

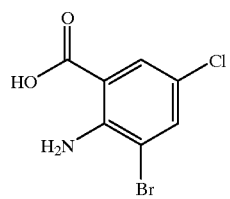

7 ii) iodonating the compound of formula 7 to obtain 2-iodo-3-bromo-5-chlorobenzoic acid of formula 8

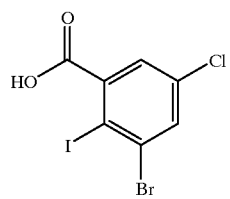

8 iii) reducing the carboxylic acid of the halo-substituted benzoic acid of formula 8 to obtain the corresponding hydroxy-methyl compound of formula 9

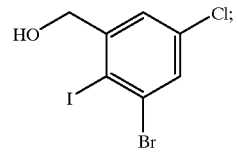

9 and iv) brominating the compound of formula 9.

Also claimed herein is a process for preparing a compound of formula 5A

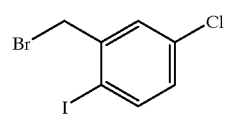

5A comprising:

i) iodonating the compound of formula 7A

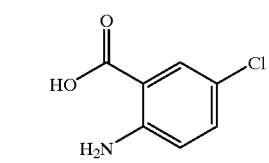

7A to obtain 2-iodo-5-chlorobenzoic acid of formula 8A

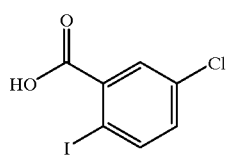

8A ii) reducing the carboxylic acid of the halo-substituted benzoic acid of formula 8A to obtain the corresponding hydroxy-methyl compound of formula 9A

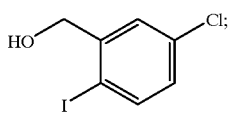

9A and iii) brominating the compound of formula 9A.

Preferred compounds of formula I are those wherein $R^2$ is halo. Also preferred are compounds wherein $R^1$ and $R^3$ are each hydrogen. Another group of preferred compounds is that wherein R, $R^1$, $R^3$ and $R^4$ are hydrogen and $R^2$ is halo. Still another group of preferred compounds is that wherein $R^1$ and $R^3$ are each hydrogen and R and $R^2$ are independently selected from the group consisting of halo. Yet another group of preferred compounds is that wherein $R^1$ and $R^3$ are each hydrogen and R, $R^2$ and $R^4$ are independently selected from the group consisting of halo. Halo is preferably Cl or Br.

DETAILED DESCRIPTION

As used herein, the terms "alkyl" and "lower alkyl," where not otherwise defined, mean straight or branched alkyl chains of 1 to 6 carbon atoms.

"Halo" refers to fluorine, chlorine, bromine or iodine radicals.

"Aryl" means phenyl, substituted phenyl wherein the substituents are 1 to 3 substituents independently selected from the group consisting of $C_1$ to $C_6$ alkyl and $C_1$ to $C_6$ alkoxy, benzyloxy or naphthyl.

"Heteroaryl" means a 5- or 6-membered aromatic ring comprising one or two nitrogen atoms, e.g., pyridyl, pyrimidyl, imidazolyl or pyrrolyl.

When $R^5$ and $R^6$, together with the nitrogen to which they are attached, form a ring comprising 4 to 6 carbon atoms, the rings so produced are exemplified by pyrrolidinyl, piperidinyl and perhydroazepine. When $R^5$ and $R^6$, together with the nitrogen to which they are attached, form a ring comprising 4 to 5 carbon atoms and a heteroatom, the rings so produced are exemplified by piperazinyl, N-methyl-piperazinyl, N-phenyl-piperazinyl and morpholinyl.

The compounds prepared by the process disclosed above are useful as intermediates in the procedures described in PCT/US96/19603 and U.S. Pat. No. 5,151,423 to obtain the desired compounds wherein the piperidinyl ring is N-substituted. Using those procedures, the compounds of the present invention are reacted with a substituted piperidine of the formula

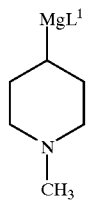

wherein $L^1$ is a leaving group selected from the group consisting of Cl and Br, to obtain a compound of the formula

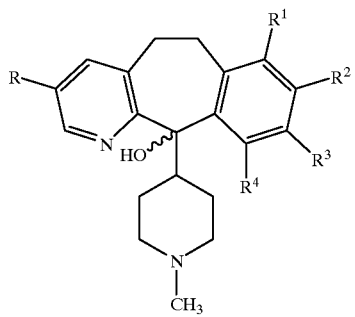

This compound is converted to the corresponding piperidylidene, the nitrogen is deprotected, and the compound is reduced to the piperidyl form. The piperidinyl nitrogen can then be reacted with a variety of compounds, e.g., an acyl compound such as an ester or acyl chloride to form the desired amide.

By using the intermediates prepared by the process of this invention, the desired tricyclic antihistamines and FPT inhibitors described above can be made by a seven-step process rather than the fifteen-step process disclosed in the art. The present process allows halo substitution at any of $R^1$, $R^2$, $R^3$ and/or $R^4$, while previously disclosed procedures were not operative for preparing compounds wherein $R^4$ is halogen. Moreover, the present process, employing the iodo-substituted intermediate of formula 3, is regioselective, producing the compound of formula 4 in high yield; without the iodo substituent, the reaction of step (b) produces undesirable mixtures of products, for example compounds wherein two compounds of formula 2 react in the presence of the strong base to produce a compound wherein the methyl group of one molecule joins to the carbonyl group of the other.

In step (a), the bromo-substituted pyridine of formula 1 is reacted with the amine $NHR^5R^6$ or with the alcohol of formula $R^{10}OH$ in the presence of a palladium catalyst, carbon monoxide (CO) and a base; when reacted with the alcohol, the product is then converted to an amide by reaction with an amine of the formula $NHR^5R^6$.

As defined above, the amines of formula $NHR^5R^6$ are exemplified by aniline, N-methylaniline, pyrrolidine, piperidine, perhydroazepine, piperazine, N-methyl-piperazine, N-phenyl-piperazine and morpholine. Preferred amines are aniline and N-methylaniline, with aniline being most preferred. The amount of amine ($NHR^5R^6$) reacted ranges from 1 to 4 equivalents, and is preferably 1 to 1.5 equivalents.

Palladium catalysts are exemplified by $PdX_2$/ligand at ratios of 1:0.5 to 1:3, preferably 1:1 to 1:2, at a range of 0.5 to 40 mol %, preferably 1 to 10 mol %, and most preferably 1 to 5 mol %; $Pd(PPh_3)_4$; $(R^{11})_3P/Pd_2(dba)_3$; and Pd/C, wherein X is OAc or Cl, ligand refers to $P(R^{11})_3$ or a nitrogen-based ligand such as dipyridyl, 2-aminopyridine, 2-cyanopyridine, 2-dimethylaminopyridine, 1,10-phenanthroline, 2-methoxypyridine or (S)-(−)-nicotine, and wherein Ac is acetyl, $R^{11}$ is $C_1$ to $C_6$ alkyl or aryl, Ph is phenyl, and dba is dibenzylidene acetone. Preferred catalysts are $Pd(OAc)_2$/dipyridyl, $Pd(OAc)_2/P(R^{11})_3$ and $(PPh_3)_2PdCl_2$.

Suitable bases include, but are not limited to, $C_1$ to $C_{10}$ alkyl amines such as triethylamine ($Et_3N$), t-butylamine and 1,8-diazabicyclo-[5,4,0]undec-7-ene (DBU), and inorganic bases such as $K_2CO_3$, $Na_2CO_3$, $Na_2HPO_4$ and NaOH. Preferred bases are $K_2CO_3$, DBU and $Et_3N$, with 1,8-DBU being preferred for use with $Pd(OAc)_2$/dipyridyl and $Et_3N$ being preferred for use with $(PPh_3)_2PdCl_2$.

Suitable solvents are tetrahydrofuran (THF), dimethylformamide (DMF), acetonitrile ($CH_3CN$) and toluene or a combination thereof. $CH_3CN$ is preferred for reaction with an amine and a combination of $CH_3CN$ and toluene is preferred for reaction with an alcohol. The temperature range for the reaction is 35° C. to 100° C., preferably about 55° C. for reaction with the amine and preferably about 80° C. for reaction with an alcohol. The reaction is carried out at a pressure of 5 psi to 500 psi, preferably 40 to 200 psi, and most preferably at 50 to 150 psi. The time for reaction ranges from 2 hours to 4 days, preferably 4 hours to 2 days, and most preferably 16 to 48 hours.

Conversion of the ester of formula 2A to the amide of formula 2 is accomplished by methods well known in the art, for example by reacting the ester directly with the amine or by using the conditions described by Basha et al in *Tetrahedron Letters*, (1977), p. 4171.

In step (b), the amide formed in step (a) is reacted with the iodo-substituted compound of formula 3 in a solvent such as THF, t-butyl methyl ether (t-BuOMe), diethyl ether (Et$_2$O), diglyme or a mixture thereof, preferably a mixture of THF and t-butyl methyl ether, in the presence of a strong base such as lithium diisopropylamide (LDA), lithium hexamethyidisilylamide or soium amide, preferably LDA. The concentration of the base ranges from 2.0 to 4.0 equivalents, preferably 2.0 to 2.2 equivalents. The iodo compound of formula 3 is reacted in a concentration range of 1.0 to 1.5 equivalents, preferably 1.1 equivalents. The reaction is carried out in a temperature range of −78° C. to −20° C., preferably −50° C. to −30° C.

In step (c), the product of step (b) is cyclized by treating with 1.0 to 3.0 equivalents, preferably 1.1 equivalents, of a reagent of the formula R$^8$MgL, wherein R$^8$ is C$_1$–C$_6$ alkyl such as iso-propyl; aryl such as phenyl, 2,4,6-trimethylphenyl, 2-methylphenyl, 2-methoxy-phenyl, 2-methoxy-5-methylphenyl or 2,5-dimethoxyphenyl; or heteroaryl such as N-methyl-piperidyl and L is Br or Cl. Typical reagents of the formula R$^8$MgL are isopropylmagnesium chloride, 2-mesitylmagnesium bromide, o-tolyl-magnesium bromide, 2-methoxy-phenylmagnesium bromide, 2-methoxy-5-methylphenylmagnesium bromide, 2,5-dimethoxyphenyl-magnesium bromide and N-methyl-piperidylmagnesium bromide. A preferred reagent of formula R$^8$MgL is one wherein R$^8$ is 2-methoxy-phenyl, e.g., 2-methoxyphenylmagnesium bromide. For compounds wherein none of R, R$^1$, R$^2$, R$^3$ and R$^4$ are bromo, the cyclization reagent can also be R$^8$Li, wherein R$^8$ is as defined above. Preferred R$^8$Li reagents are n-, sec- and tert-butyllithium, methyllithium and phenyllithium. Suitable solvents include t-BuOMe, Et$_2$O, THF and toluene, with THF being preferred. The temperature range for the reaction is −78° C. to 25° C., preferably 0 to −40° C., and most preferably −25 to −15° C.

Before cyclization, a protecting step is necessary when one of R$^5$ or R$^6$ is hydrogen. A protecting group can be added either after step (a) or after step (b). A compound of formula 2 or 4 is suitably protected by methods well known in the art, for example by reacting with CH$_3$I and a base such as NaNH$_2$, LDA, butyl lithium, NaH, CaH$_2$ or NaOH with a phase transfer cataylst, preferably NaH or NaOH with a phase transfer cataylst. Suitable phase transfer catalysts include C$_1$ to C8 tertiary alkyl amine salts such as tetrabutylammonium bromide, tetrabutylammonium chloride or tetraoctylammonium bromide, benzyltriethylammonium chloride, trialkylsulfates, phosphorus salts and crown ethers. Base concentration ranges from 1 to 3 equivalents, preferably 1.5 equivalents, and phase transfer catalyst concentration ranges from 1.0 to 50 mol %, preferably 10 mol %. CH$_3$I concentration ranges from 1.0 to 5 equivalents, preferably 1.5 equivalents. Suitable solvents for the methylation step are THF, DMF, N,N-dimethyl-acetamide and dimethylsulfoxide (DMSO), with DMF being preferred. The temperature range for the reaction is −20° C. to 20° C., preferably −10° C.

In the process for preparing the intermediate of formula 5, step (i) comprises brominating an amino, halo-substituted benzoic acid of formula 6 to obtain the corresponding 3-bromo-substituted benzoic acid of formula 7 by treating the compound of formula 6 with 1.0 to 2.0 equivalents, preferably 1.5 equivalent of bromine and an acid such as acetic acid (HOAc), HCl, CF$_3$CO$_2$H, CH$_3$SO$_3$H or CF$_3$SO$_3$H, preferably HOAc. The reaction is carried out at a temperature of 0 to 40° C., preferably 10 to 20° C.

In step (ii), the brominated benzoic acid of formula 7 is iodinated to obtain a compound of formula 8 by reacting with NaNO$_2$ or KNO$_2$, preferably NaNO$_2$, in an acid such as HCl, H$_2$SO$_4$, CH$_3$SO$_3$H or CF$_3$CO$_2$H, preferably H$_2$SO$_4$, and then treating the resultant product with Kl, Nal or tetrabutylammonium iodide, preferably Kl, in water. The nitrite concentration ranges from 1.0 to 4.0 equivalents, preferably 2.2 equivalents, and the iodide concentration ranges from 2 to 10 equivalents, preferably 5 to 7 equivalents. The reaction temperature ranges from −10 to 40° C., with a preferred range of −5 to 50° C.

In step (iii), the chloro-bromo-iodo benzoic acid of formula 8 is reduced to the corresponding alcohol by methods well known in the art. Suitable reducing agents include, but are not limited to, BH$_3$.THF and B(OCH$_3$)$_3$, BH$_3$.(CH$_3$)$_2$S (BMS) and B(OCH$_3$)$_3$, NaBH$_4$/SOCl$_2$, KBH4/SOCl$_2$, NaBH4/AlCl$_3$ and NaBH4TiCl$_4$. Preferred reagents are BH$_3$.THF or BMS in combination with B(OCH$_3$)$_3$ or NaBH$_4$ in combination with SOCl$_2$. As an example, the concentration of BMS ranges from 1.0 to 4.0 equivalents, preferaby 2.5 to 3.0 equivalents, and the concentration of B(OCH$_3$)$_3$ ranges from 5 to 20 equivalents, preferably 10 to 16 equivalents. The temperature range for the reaction is from 0 to 30° C., preferably 15 to 25° C.

In step (iv) of the process for preparing the intermediate, the hydroxysubstituted compound is converted to the corresponding bromo-substituted compound by treatment with a brominating reagent such as SOBr$_2$, PPh$_3$ and Br$_2$, or Br$_3$P, preferably PPh$_3$ and Br$_2$. The amount of PPh$_3$ and Br$_2$ ranges from 1.0 to 2.0 equivalents, preferably being 1.1 to 1.4 equivalents. Suitable solvents are THF, CH$_3$CN, EtCN and CH$_2$Cl$_2$, with CH$_3$CN being preferred. The temperature range for the reaction is 0 to 20° C., preferably 3 to 8° C.

In the process for preparing the intermediate of formula 5A, the benzoic acid of formula 7A is iodinated to obtain a compound of formula 8A, reduced to the alcohol of formula 9A, and brominated in the same manner as that described for the preparation of the compound of formula 5.

Starting materials of formula 1, NHR$^5$R$^6$, R$^8$MgL and R$^8$Li are known in the art or can readily be prepared by one skilled in the art. Starting materials of formula 3 are known in the art or, where the starting material is of formula 5 or 5A, can be prepared by methods disclosed herein.

Following are specific examples of the procedures in the various steps of the process of this invention for preparing compounds of formula 1 and formula 3, although those skilled in the art will appreciate that similar procedures within the scope of the process of this invention can be used to prepare other compounds of formula 1 and formula 3.

Preparation 1

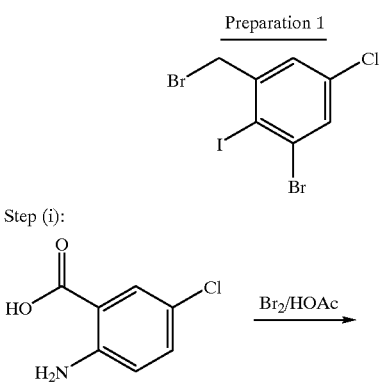

Step (i): Br$_2$/HOAc

-continued

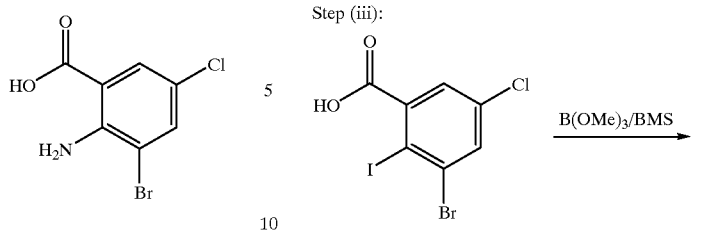

To a solution of 200 g (1.05 mol) of 2-amino-5-chlorobenzoic acid in 3.4 L of HOAc at 15° C. was added dropwise 184 g (1.15 mol) of Br2. The mixture was stirred at 15° C. for 4 hrs, quenched slowly into 8 L of water, and extracted with 2×2 L of t-BuOMe. The combined extract was washed with water, dried over $MgSO_4$ and concentrated. The crude product was treated with hot hexane, filtered and dried to give 210 g (80%) of 2-amino-3-bromo-5-chlorobenzoic acid as white solid. Mp. 225–2280° C. $^1$H NMR (DMSO-$d_6$): δ7.70 (d, J=2.6 Hz, 1 H), 7.69 (d, J=2.6 Hz, 1 H), 6.8 (bs, 2 H). $^{13}$C NMR (DMSO-$d_6$): δ168.16, 147.06, 136.25, 130.19, 118.22, 112.35,110.34. IR:3480 (m), 3350 (m), 2920 (s), 1670 (s) cm$^{-1}$. Analysis calcd. for $C_7H_5BrClNO_2$: C, 33.53, H, 2.00, N, 5.59; Found: C, 33.63, H, 2.12, N, 5.70.

Step (ii):

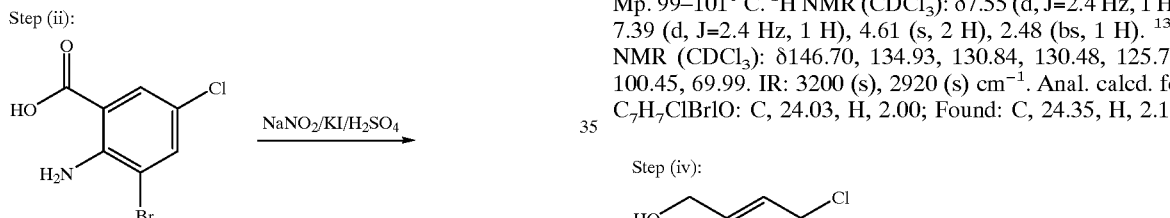

To 40 g (159 mmol) of the product of step (i) in 160 mL of conc. $H_2SO_4$ at 0° C. 24.1 g (350 mmol) of $NaNO_2$ was added slowly. The mixture was mechanically stirred at that temperature for 3 hrs and quenched into 1 L ice with strong agitation. The resulting solution was added slowly into 158 g (954 mmol) of KI in 2 L ice water and extracted with 2×1 L of EtOAc. The combined extract was washed with $NaHSO_3$, dried over $MgSO_4$ and concentrated. To the residue was added hexane and the precipitate was filtered and dried to give 50.4 g (87%) of 2-Iodo-3-bromo-5-chlorobenzoic acid as white solid. Mp. 174–176° C. $^1$H NMR (DMSO-$d_6$): δ7.98 (d, J=2.4 Hz, 1 H), 7.60 (d, J=2.4 Hz, 1 H). $^{13}$C NMR (DMSO-d6): δ168.08, 144.23, 134.13, 133.08, 132.53, 126.91, 99.88. IR: 3150 (m), 2920 (s), 1720 (s), 1650 (m) cm$^{-1}$.

Step (iii):

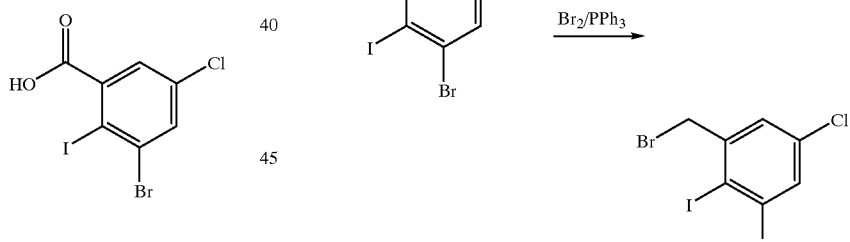

To a 2 L flask with a mechanical stirrer, a thermometer, and an addition funnel, at r.t. were added sequentially 50 g (138 mmol) of the product of step (ii), 500 mL of THF, 229 mL (2.01 mol) of 2.0 M $(CH_3O)_3B$ and 193 mL (386.4 mmol) of 2.0 M $BH_3.(CH_3)_2S$. The reaction mixture was stirred at r.t. for 18 hrs, quenched with 500 mL of $CH_3OH$ and concentrated. The residue was dissolved with 1 L EtOAc, washed with brine, dried over $MgSO_4$, and concentrated to give 47 g (98%) of 2-iodo-3-bromo-5-chlorobenzyl alcohol as a white solid.

Alternatively, the acid was reduced following a two-step, one-pot procedure: first, the acid was converted to its corresponding acid chloride and then treated with $NaBH_4$. Mp. 99–101° C. $^1$H NMR ($CDCl_3$): δ7.55 (d, J=2.4 Hz, 1 H), 7.39 (d, J=2.4 Hz, 1 H), 4.61 (s, 2 H), 2.48 (bs, 1 H). $^{13}$C NMR ($CDCl_3$): δ146.70, 134.93, 130.84, 130.48, 125.74, 100.45, 69.99. IR: 3200 (s), 2920 (s) cm$^{-1}$. Anal. calcd. for $C_7H_7ClBrIO$: C, 24.03, H, 2.00; Found: C, 24.35, H, 2.19.

Step (iv):

To a 500 mL flask with a mechanical stirrer at 5° C. were added 9.7 g (37 mmol) of $PPh_3$, 100 mL $CH_3CN$ and 6 g (37 mmol) of $Br_2$. The reaction mixture was stirred at 5° C. for 1 hr, and 10 g (28.7 mmol) of the alcohol of step (iii) in 100 mL of $CH_3CN$ was added dropwise. The reaction mixture was allowed to warm to r.t., agitated for 1 hr, and concentrated. The residue was extracted with 2×400 mL $CH_2Cl_2$, washed with brine, dried over $MgSO_4$ and concentrated. The phosphoxide was filtered after addition of hexane. The filtrate was passed through a pad of silca gel and concentrated to give 11.3 g (96%) of 2-iodo-3-bromo-5-chlorobenzylbromide as a white solid.

Alternatively, the alcohol was converted either to the bromide using $SOBr_2$ in 90% yield, or to the corresponding chloride using $SOCl_2$. Mp. 75–77° C. $^1$H NMR ($CDCl_3$): δ7.54 (d, J=2.4 Hz, 1 H), 7.36 (d, J=2.4 Hz, 1 H), 4.60 (s, 2 H). $^{13}$C NMR (CDCl$_3$): δ 143.94, 134.66, 131.98, 131.58, 128.15, 104.71, 39.52. IR: 2920 (s), 1540 (m) cm$^{-1}$.

Preparation 2

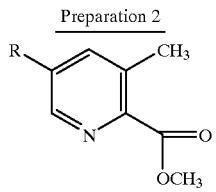

To a 400 mL autoclave was charged 1.6 g (6.06 mmol) of 2,5-dibromo-3-methylpyridine, 0.45 g (0.64 mmol) of (PPh$_3$)$_2$PdCl$_2$, 30 mL of toluene/CH$_3$CN (1:1), 0.33 mL (95 mmol) of Et$_3$N and 4 eq. of CH$_3$OH. The autoclave was sealed, evacuated, flushed with nitrogen three times and charged with carbon monoxide to 80 psi. The autoclave was heated to 80° C. for 16 hrs, cooled to r.t. and the excess carbon monoxide was evacuated under vacuum. The conversion was about 55% as determined by NMR. The contents of the autoclave were transferred into a flask for concentration. The residue was then purified on a silica gel column, eluting with hexane:EtOAc to give the ester as a white solid. M.p. 61–62° C. $^1$H NMR (CDCl$_3$): δ8.58 (d, J=1.9 Hz, 1 H), 7.78 (d, J=1.9 Hz, 1 H), 3.96 (s, 3H), 2.58 (s, 3 H). $^{13}$C NMR (CDCl$_3$): δ165.82, 147.94, 145.17, 142.20, 137.63, 123.56, 52.74, 19.96. IR: 1715 cm$^{-1}$.

Preparation 3

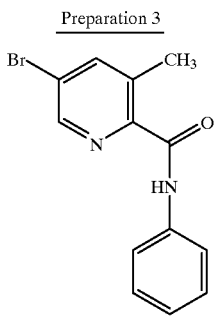

To a 4 L autoclave were added sequentially 250 g (949 mmol) of 2,5-dibromo-3-methylpyridine, 6.7 g (30 mmol) of Pd(OAc)$_2$, 5.0 g (32 mmol) of dipyridyl, 10 L of toluene, 127 mL (1.1 mol) of aniline, and 277 mL (2.0 mol) of DBU. The autoclave was sealed, evacuated, purged with nitrogen, and charged with carbon monoxide to 80 psi. The reaction mixture was heated to 65° C. for about 2 days with periodical refilling as necessary, and then cooled to r.t. The contents of the autoclave was vented under vacuum and flushed with nitrogen, then transferred to a 10 L flask with the aid of water and EtOAc. The mixture was concentrated and filtered through a pad of celite. The filtrate was extracted with 2×1 L of toluene. The combined extract was washed with brine, filtered and concentrated. The residue was recrystallized from hot i-PrOH and the precipitate was filtered, washed with M.L., and dried at 50° C. to give 220 g (76%) of the amide as white solid.

Preparation 4

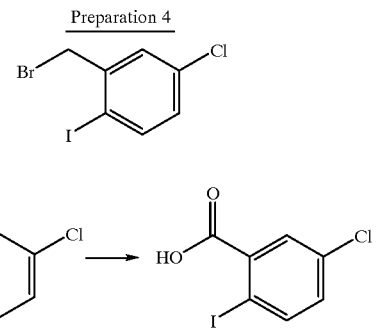

Step (i):

To 75 g (394 mmol) of 2-amino-5-chlorobenzoic acid (90%) in 300 mL of conc. H$_2$SO$_4$ at 0° C. was added slowly 60 g (870 mmol) of NaNO$_2$. The mixture was mechanically stirred at that temperature for 5 hrs and at rt for 12 hrs, then quenched into 2 L ice with strong agitation. The resulting solution was added slowly into 393 g (2.37 mol) of KI in 2 L ice water and extracted with 2×1 L of EtOAc. The combined extract was washed with NaHSO$_3$, dried over MgSO4, concentrated and dried to give 124 g (>100%) of 2-iodo-5-chlorobenzoic acid as white solid. $^1$H NMR (DMSO-d$_6$): δ7.91 (d, J=8.5 Hz, 1 H), 7.66 (d, J=2.6 Hz, 1 H), 7.26 (dd, J=8.5, 2.6, 1 H).

Step (ii):

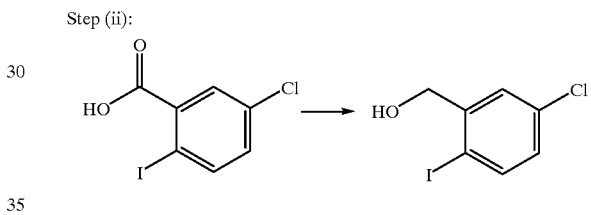

To a 2 L flask with a mechanical stirrer, a thermometer, and an addition funnel at r.t. were added sequentially 124 g (0.4 mol) of the product of Step (i), 700 mL of THF, 500 g (4.85 mol) of (CH$_3$O)$_3$B, and 560 mL (1.12 mol) of 2.0 M BH$_3$.Me$_2$S. The reaction mixture was stirred at r.t. for 18 hrs., quenched with 500 mL of CH$_3$OH and concentrated. The residue was dissolved with 1 L EtOAc, washed with brine, dried over MgSO4, and concentrated to give 121 g (>100%) of 2-iodo-5-chlorobenzyl alcohol as white solid. $^1$H NMR (CDCl$_3$): δ7.64 (d, J=8.3 Hz, 1 H), 7.41 (d, J=2.5 Hz, 1 H), 6.93 (dd, J=8.3, 2.5, 1 H), 4.57 (s, 2H).

Step (iii):

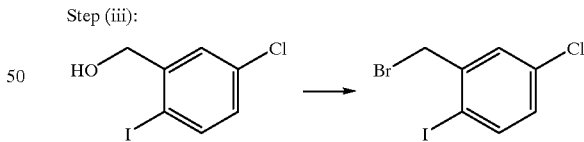

To a 500 mL flask with a mechanical stirrer at 5° C. were added 140 g (0.53 mol) of PPh$_3$, 1100 mL CH$_3$CN, and 85 g (0.53 mol) of Br$_2$. The reaction mixture was stirred at 5° C. for 1 hr, and 121 g (about 0.4 mmol) of the alcohol of Step (ii) was added portionwise. The reaction mixture was allowed to warm to r.t., agitated for 1 hr, and concentrated. The residue was extracted with 2×400 mL CH$_2$Cl$_2$, washed with brine, dried over MgSO$_4$, and concentrated. The phosphoxide was filtered after addition of hexane. The filtrate was passed through a pad of silica gel and concentrated to give 2-iodo-5-chlorobenzylbromide as white solid (about 95% yield). $^1$H NMR (CDCl$_3$): δ7.68 (d, J=8.5 Hz, 1 H), 7.38 (d, J=2.5 Hz, 1 H), 6.90 (dd, J=8.5, 2.5 Hz, 1 H), 4.44 (s, 2H).

Example 1

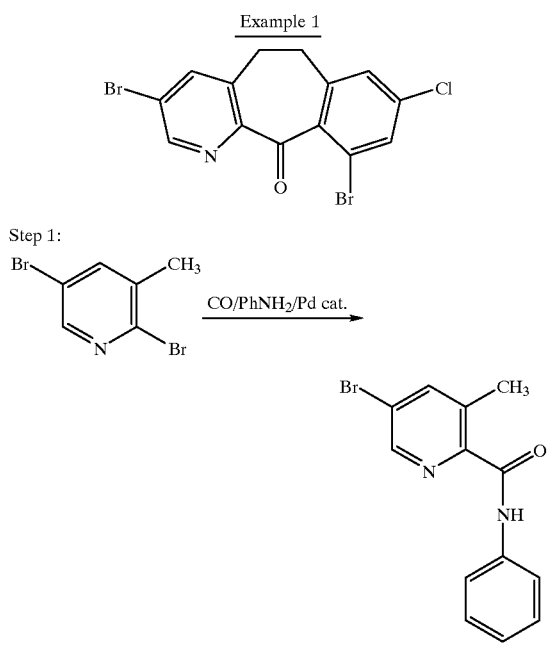

Step 1:

To a 4 L autoclave were added sequentially 250 g (949 mmol) of 2,5-dibromo-3-methylpyridine, 21 g (30 mmol) of (Ph$_3$P)$_2$PdCl$_2$, 2 L of CH$_3$CN, 100 mL (1.1 mol) of aniline, and 154 mL (1.5 mol) of Et$_3$N. The autoclave was sealed, evacuated, purged with nitrogen and charged with carbon monoxide to 80 psi. The reaction mixture was heated to 60° C. for about 3 days with periodical refilling as necessary, and then cooled to r.t. The contents of the autoclave was vented under vacuum, flushed with nitrogen and transferred to a 10 L flask with the aid of water and EtOAc. The mixture was concentrated and filtered through a pad of celite. The filtrate was extracted with 2×1 L of EtOAc. The combined extract was washed with brine, dried over MgSO$_4$, filtered and concentrated. The residue was recrystallized from hot i-PrOH and the precipitate was filtered, washed with mother liquor and dried at 50° C. to give 162 g (59%) of the amide as white solid. The solution yield was determined to be 71%. Mp. 103–104° C. $^1$H NMR (CDCl$_3$): δ10.00 (bs, 1 H), 8.49 (d, J=2.1 Hz, 1 H), 7.79 (d, J=2.1 Hz, 1 H), 7.72 (d, J=7.5 Hz, 2H), 7.37 (dd, J=7.5, 7.4 Hz, 2 H), 7.13 (t, J=7.4 Hz, 1 H), 2.79 (s, 3 H). $^{13}$C NMR (CDCl$_3$): δ162.79, 146.34, 145.21, 143.29, 137.91, 137.72, 128.96, 124.18, 123.12, 119.61, 20.68. IR: 3320 (w), 2920 (s), 1700 (m) cm$^{-1}$. Elemental analysis: calcd for C$_{13}$H$_{11}$BrN$_2$O: C, 53.60, H, 3.78, N, 9.62; found: C, 53.50, H, 3.79, N, 9.51.

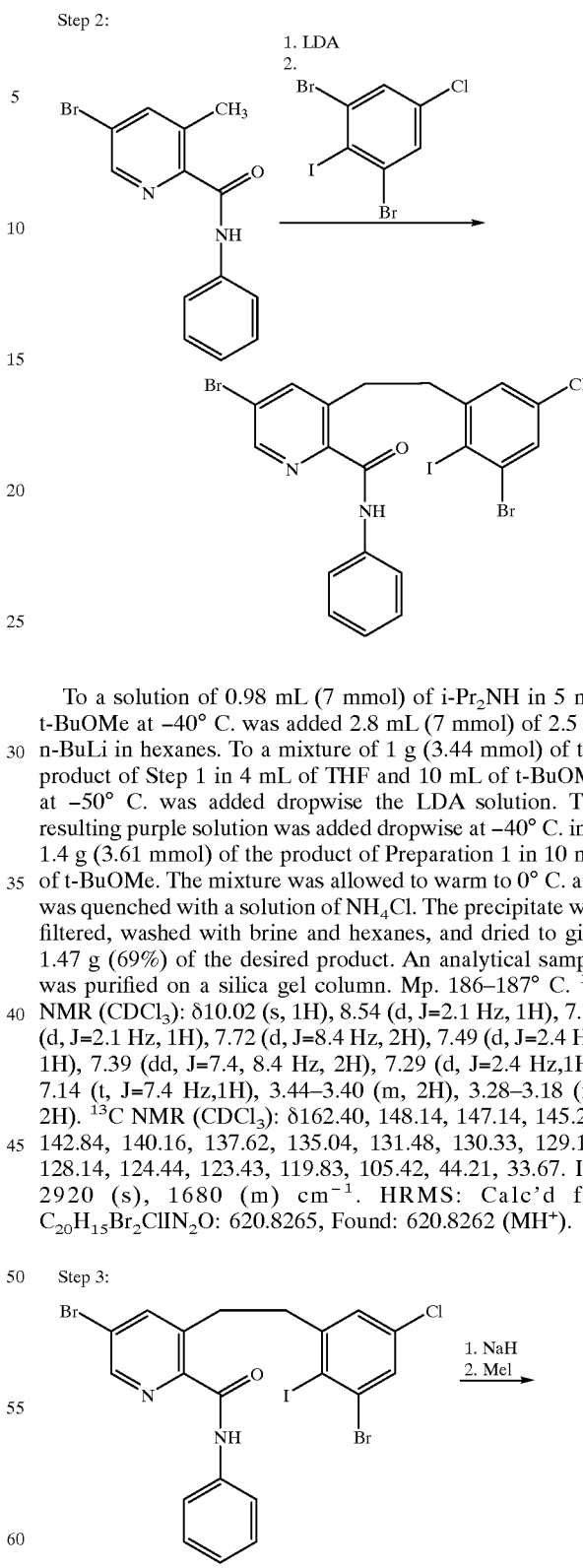

To a solution of 0.98 mL (7 mmol) of i-Pr$_2$NH in 5 mL t-BuOMe at −40° C. was added 2.8 mL (7 mmol) of 2.5 M n-BuLi in hexanes. To a mixture of 1 g (3.44 mmol) of the product of Step 1 in 4 mL of THF and 10 mL of t-BuOMe at −50° C. was added dropwise the LDA solution. The resulting purple solution was added dropwise at −40° C. into 1.4 g (3.61 mmol) of the product of Preparation 1 in 10 mL of t-BuOMe. The mixture was allowed to warm to 0° C. and was quenched with a solution of NH$_4$Cl. The precipitate was filtered, washed with brine and hexanes, and dried to give 1.47 g (69%) of the desired product. An analytical sample was purified on a silica gel column. Mp. 186–187° C. $^1$H NMR (CDCl$_3$): δ10.02 (s, 1H), 8.54 (d, J=2.1 Hz, 1H), 7.78 (d, J=2.1 Hz, 1H), 7.72 (d, J=8.4 Hz, 2H), 7.49 (d, J=2.4 Hz, 1H), 7.39 (dd, J=7.4, 8.4 Hz, 2H), 7.29 (d, J=2.4 Hz,1H), 7.14 (t, J=7.4 Hz,1H), 3.44–3.40 (m, 2H), 3.28–3.18 (m, 2H). $^{13}$C NMR (CDCl$_3$): δ162.40, 148.14, 147.14, 145.20, 142.84, 140.16, 137.62, 135.04, 131.48, 130.33, 129.10, 128.14, 124.44, 123.43, 119.83, 105.42, 44.21, 33.67. IR: 2920 (s), 1680 (m) cm$^{-1}$. HRMS: Calc'd for C$_{20}$H$_{15}$Br$_2$ClIN$_2$O: 620.8265, Found: 620.8262 (MH$^+$).

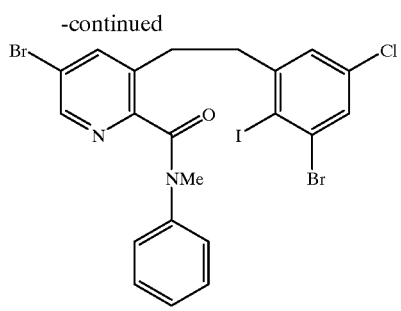

To 27.7 g (44.2 mmol) of the product of Step 2 in 750 mL of DMF at −10° C. was added 1.5 g 80% NaH (66.3 mmol). After stirring at −100° C. for 1 hr, 4.1 mL (66.3 mmol) of CH₃I was added to the flask. The mixture was mechanically stirred at −10° C. for 1 hr, then quenched carefully into 2 L ice. The precipitate was filtered, washed with water and dried to give 23.7 g (85%) of the desired product as an off-white solid. Mp. 180–181° C. NMR indicates two rotamers. $^1$H NMR (CDCl₃): δ8.26 (d, J=1.8 Hz, 1H), 7.53 (d, J=1.8 Hz, 1H), 7.52 (s, 1H), 7.18–7.10 (m, 6H), 3.15 (s, 3H), 3.17–3.10 (m, 2H), 2.83–2.79 (m, 2H). $^{13}$C NMR (CDCl₃): δ167.61, 152.35, 147.94, 147.59, 142.87, 139.41, 135.11, 131.79, 130.51, 129.06, 129.04, 127.98, 127.04, 126.65, 120.21, 105.08, 43.97, 37.26, 31.96. IR: 2920 (s), 1650 (m) cm$^{-1}$. HRMS: Calc'd for $C_{21}H_{17}Br_2ClIN_2O$: 634.8420, Found: 634.8423 (MH⁺).

Step 4:

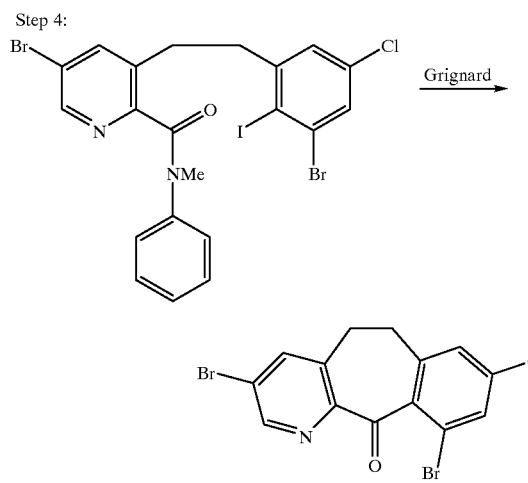

To a solution of 2 g (3.15 mmol) of the product of Step 3 in 40 mL of THF at −20° C. was added dropwise 4.8 mL of 0.72 M 2-CH₃OC₆H₄MgBr (3.5 mmol) in THF. The mixture was stirred at −200° C. for 20 min. and quenched with 5 mL of saturated NH₄Cl. The quenched solution was stirred at r.t. for 16 hrs. to complete the hydrolysis, concentrated and extracted with 2×10 mL of EtOAc. The combined extract was washed with brine, dried over MgSO₄ and concentrated. The residue was chromatographed on silica gel, eluting with hexane/EtOAc (9:1) to give 0.84 g (66%) of the azoketone. The solution yield was determined to be 82% by HPLC. Mp. 198–200° C. $^1$H NMR (CDCl₃): δ8.74 (d, J=1.8 Hz, 1 H), 7.75 (d, J=1.8 Hz, 1 H), 7.55 (d, J=1.8 Hz, 1 H), 7.20 (d, J=1.8 Hz, 1 H), 3.25–3.19 (m, 2 H), 3.15–3.09 (m, 2 H). $^{13}$C NMR (CDCl₃): δ194.17, 150.21. 149.39, 140.90, 140.73, 139.18, 137.69, 136.54, 131.48, 126.79, 123.33, 119.88, 32.78, 31.59. IR: 2920 (s), 1690 (m) cm$^{-1}$. Elemental analysis: Calcd. for $C_{14}H_8Br_2ClNO$: C, 41.84, H, 1.99, N, 3.49; Found: C, 42.11 H, 2.07, N, 3.64.

Example 1A

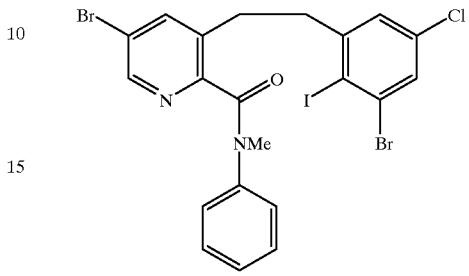

Alternative route to the product of Example 1, Step 3:

Br—[pyridine]—CH₃ with N-methyl amide, phenyl   1. LDA   2. ZnBr₂   3. Br—CH₂—[aryl Cl, I, Br]   →   [product]

To a solution of 2.5 mL (18 mmol) of diisopropylamine in 10 mL dry THF at −60° C. was added dropwise 7.2 mL (18 mmol) of 2.5 M n-BuLi. To another flask containing 5 g (16.4 mmol) of the N-methyl amide starting material (prepared in a manner similar to that described in Example 1, Step 1) in 50 mL THF at −78° C. was added the above LDA solution. After stirring at −78° C. for 5 min., 20.8 mL (18 mmol) of a freshly prepared solution of ZnBr₂ was added. To the resulting mixture was added 6.7 g (16.4 mmol) of 5-chloro-3-bromo-2-2iodobenzyl bromide in 10 mL THF. The reaction was heated to reflux for 2 hrs, quenched slowly into saturated NH₄Cl and extracted with toluene. The combined extract was washed with brine, dried over MgSO₄ and concentrated. The precipitate was filtered to give 4.6 g (44%) of the N-methylated product. The HPLC solution yield was determined to be 60%.

17

Step 1:

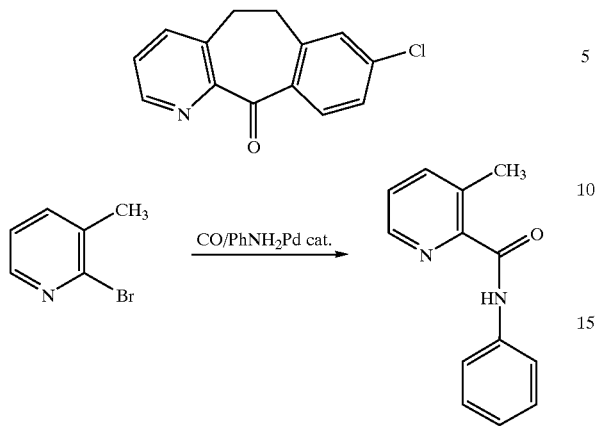

In a 150 mL autoclave were added sequentially 10 g (55 mmol) of 2-bromo-3-methylpyridine, 1.2 g (1.7 mmol) of $(Ph_3P)_2PdCl_2$, 50 mL of $CH_3CN$, 8 mL (87 mmol) of aniline, and 18 mL (116 mmol) of DBU. The autoclave was sealed, evacuated, purged with nitrogen and charged with carbon monoxide to 80 psi. The reaction mixture was heated to 65° C. for 9 h with periodical refilling of carbon monoxide as necessary, and then cooled to r.t. The contents of the autoclave was vented under vacuum, flushed with nitrogen and transferred into a separatory funnel with the aid of water and EtOAc. The phases were separated and the aqueous phase was extracted with 100 mL of EtOAc. The combined extract was washed with brine, dried over $MgSO_4$, filtered and concentrated. The residue was recrystallized from hot i-PrOH and water and the precipitated was filtered and dried at 50° C. to give 6.9 g (59%) of the amide as white solid. The solution yield was determined to be 76%. Mp. 66–67° C. $^1H$ NMR ($CDCl_3$): δ10.23 (bs,1H), 8.37 (dd, J=4.6 Hz, 0.8 Hz,1H), 7.71 (m, 2H), 7.62 (dd, J=6.95 Hz,1H), 7.31–7.36 (m, 3H), 7.10 (t, J=7.42 Hz, 1H), 2.79 (s, 3H). $^{13}C$ NMR ($CDCl_3$): δ163.52, 146.70, 145.21, 141.28, 138.02, 136.13, 128.94, 125.95, 123.97, 119.62, 20.80. R: 3330 (w), 2920 (s), 1680 (m) $cm^{-1}$. Analysis. Calcd for $C_{13}H12N_2O$: C, 73.58, H, 5.66, N, 13.21; found: C, 73.29, H, 5.76, N, 12.81.

Step 2:

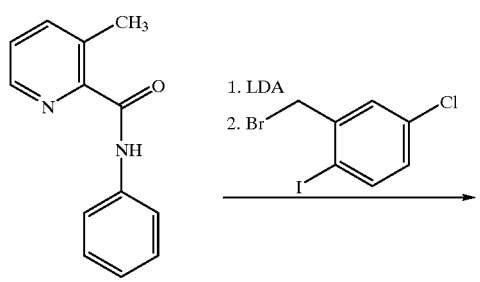

18

-continued

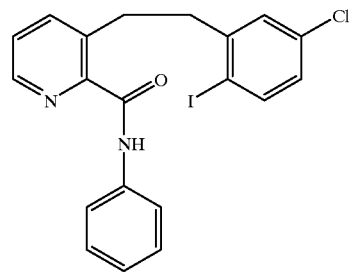

To a solution of 10 mL (70 mmol) of $i-Pr_2NH$ in 40 mL $t-BuOCH_3$ at −40° C. was added 28 mL (70 mmol) of 2.5 M n-BuLi in hexanes. To a mixture of 7.0 g (33.0 mmol) of the product of Step 1 in 30 mL of THF and 70 mL of $t-BuOCH_3$ at −30° C. was added dropwise the above LDA solution. The resulting purple solution was added dropwise at −30° C. into 11.0 g (33.0 mmol) of 3-chloro-6-iodo benzyl bromide in 20 mL of THF and 50 mL of $t-BuOCH_3$. The mixture was allowed to warm to 0° C. and quenched with a solution $NH_4Cl$. The phases were separated and the aqueous phase was extracted with 100 mL of $t-BuOCH_3$. The combined organic solution was washed with brine, dried over $MgSO_4$, filtered and concentrated. The crude product was used directly in the following step without further purification. $^1H$ NMR ($CDCl_3$): δ10.24 (s, 1H), 8.43 (dd, J=4.57 Hz, J=1.6 Hz, 1H), 7.71 (m, 2H), 7.52 (dd, J=7.8 Hz, 1,59 Hz, 1H), 7.29–7.35 (m, 2H), 7.24 (d, J=2.61 Hz,1H), 7.08 (t, J=7.43 Hz, 1H), 6.81 (dd, J=8.4 Hz, J=2.6 Hz, 1H), 3.40–3.44 (m, 2H), 3.03–3.07 (m, 2H).

Step 3:

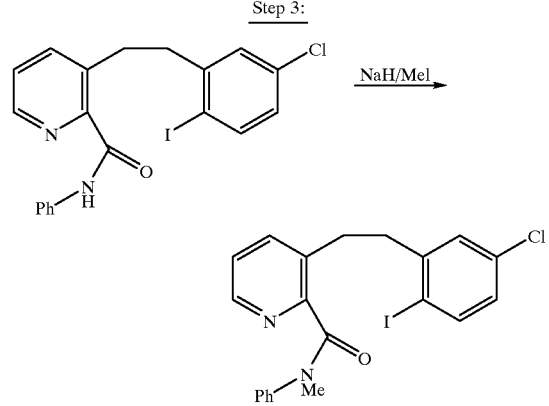

To the residue (~33 mmol) of the product of Step 2 in 70 mL of DMF at 0° C. was added 2.6 g 60% NaH (66 mmol). After stirring at 0° C. for 1 hr, 2.5 mL (40 mmol) of $CH_3I$ was added to the flask. The mixture was mechanically stirred at 0° C. for 15 min, then quenched carefully by ice. EtOAc (200 mL) was added and the solution was washed with water (100×5). The organic layer was concentrated to give 16 g residue, which was separated by column chromatography (hexane/EtOAc) to give 10 g product, 64% yield, in two steps. Mp. 106–107° C. NMR indicate two rotamers. $^1H$ NMR ($CDCl_3$): δ8.17 (d, J=4.6 Hz, 1H), 7.67 (d, J=8.5 Hz, 1H), 7.33 (d, J=7.6 Hz, 1H), 7.13 (d, J=2.4 Hz, 1H), 6.96–7.1 (m, 6H), 6.86 (dd, J=8.5, 2.4 Hz, 1H), 3.49 (s, 3H), 2.90–2.96 (m, 2H), 2.74 –2.80 (m, 2H). $^{13}C$ NMR ($CDCl_3$):

δ168.4, 153.9, 146.5, 145.4, 143.1, 140.4, 137.0, 134.6, 133.2, 129.7, 128.8, 128.3, 126.7, 126.6, 123.3, 97.2, 41.4, 37.1, 32.1.

Step 4:

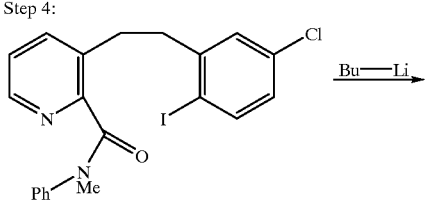

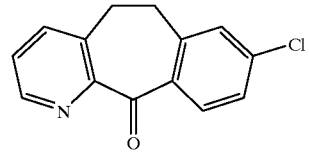

To a solution of 2 g (4.2 mmol) of the product of Step 3 in 20 mL of THF at −78° C. was added dropwise 2.52 mL of 2.0 n-BuLi (5.0 mmol) in cyclohexane. The mixture was stirred at −78° C. for 10 min. and quenched with 30 mL of saturated NH$_4$Cl. The quenched solution was extracted with 2×50 mL of EtOAc. The combined extract was washed with brine, dried over MgSO$_4$ and concentrated. The residue was passed through silica gel, eluting with hexane/EtOAc (6:4) to give 1.02 g (78%) of the title compound. $^1$H NMR (CDCl$_3$): δ8.60 (dd, J=4.6, 1.5 Hz, 1H), 7.95 (d, J=8.5 Hz, 1H), 7.55 (dd, J=7.7,1.5 Hz, 1H), 7.29 (dd, J=7.7, 4.6 Hz, 1H), 7.24 (dd, J=8.5, 2.0 Hz, 1H), 7.17 (d, J=2.0, 1H), 3.15–3.20 (m, 4H). $^{13}$C NMR (CDCl$_3$): δ194.1, 155.3, 149.4, 143.9, 139.6, 138.2, 137.4, 136.4, 133.6, 130.3, 127.9, 126.8, 35.2, 33.1.

Example 4

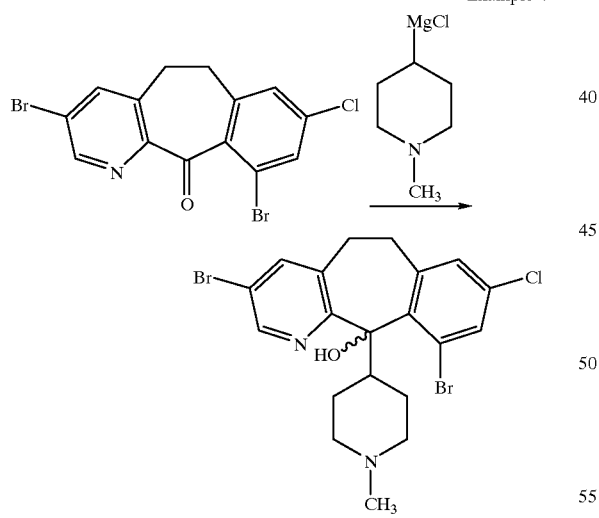

To a solution of 1.88 g (4.68 mmol) of the product of Example 1 in 10 mL THF at −20° C. was added dropwise 5.72 mL (5.15 mmol) of 0.9 M of the Grignard. The reaction was stirred at that temperature for 1 hr, quenched into NH$_4$Cl and extracted with EtOAc. The combined extract was washed with brine, dried over MgSO$_4$ and concentrated. The residue was chromatographed on silica gel, eluting with EtOAc/hexane to give 1.4 g (60%) product as fluffy solid. Mp. 98–100° C. $^1$H NMR (CDCl$_3$): δ8.45 (d, J=2.1 Hz, 1 H), 7.64 (d, J=2.1 Hz, 1 H), 7.62 (d, J=2.2 Hz, 1 H), 7.07 (d, J=2.2 Hz, 1 H), 6.86 (s, 1 H), 3.68–3.58 (m, 1 H), 3.48–3.39 (m, 1 H), 3.06–2.8 (m, 4 H), 2.66–2.57 (m, 1 H), 2.23 (s, 3 H), 1.85–1.75(m, 2 H), 1.68–1.58 (m, 1 H), 1.40–1.36 (m, 1 H), 0.91–0.85 (m, 1 H). $^{13}$C NMR (CDCl$_3$): δ156.54, 145.04, 141.25, 140.57, 139.09, 135.32, 134.65, 132.52, 130.42, 122.35, 119.64, 80.50, 56.07, 55.70, 45.94, 44.98, 34.27, 30.83, 26.20, 26.09. IR: 3300 (w), 2920 (s), 1570 (w) cm$^{-1}$.

We claim:

1. A process for preparing a compound of the formula

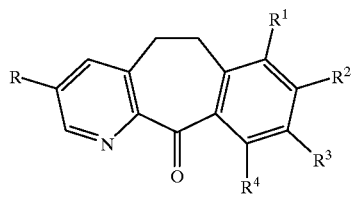

wherein:

R, R$^1$, R$^2$, R$^3$ and R$^4$ are independently selected from the group consisting of hydrogen and halo; comprising:

(a) reacting a compound of formula 1

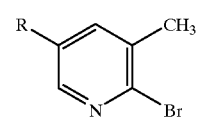

(i) with an amine of the formula NHR$^5$R$^6$, wherein R$^5$ is hydrogen and R$^6$ is C$_1$–C$_6$ alkyl, aryl or heteroaryl; R$^5$ is C$_1$–C$_6$ alkyl, aryl or heteroaryl and R$^6$ is hydrogen; R$^5$ and R$^6$ are independently selected from the group consisting of C$_1$–C$_6$ alkyl and aryl; or R$^5$ and R$^6$, together with the nitrogen to which they are attached, form a ring comprising 4 to 6 carbon atoms or comprising 3 to 5 carbon atoms and one hetero moiety selected from the group consisting of —O— and —NR$^9$—, wherein R$^9$ is H, C$_1$–C$_6$ alkyl or phenyl; in the presence of a palladium catalyst and carbon monoxide to obtain an amide of formula 2:

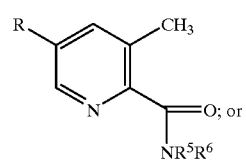

(ii) with an alcohol of the formula R$^{10}$OH, wherein R$^{10}$ is C$_1$–C$_6$ lower alkyl or C$_3$–C$_6$ cycloalkyl, in the presence of a palladium catalyst and carbon monoxide to obtain the ester of formula 2A

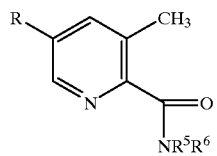

followed by reacting the compound of 2A with an amine of formula NHR$^5$R$^6$ to obtain the amide of formula 2;

(b) reacting the amide of formula 2 with an iodo-substituted compound of formula 3

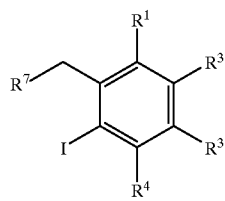

wherein R$^1$, R$^2$, R$^3$ and R$^4$ are as defined above and R$^7$ is Cl or Br, in the presence of a strong base to obtain a compound of formula 4

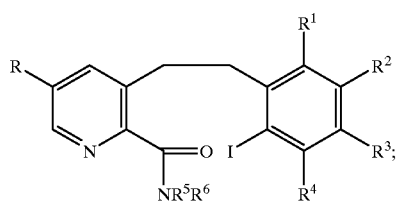

(c) cyclizing a compound of formula 4 with a reagent of the formula R$^8$MgL, or when none of R, R$^1$, R$^2$, R$^3$ and R$^4$ are bromo, with a reagent of the formula R$^8$Li, wherein R$^8$ is C$_1$–C$_8$ alkyl, aryl or heteroaryl and L is Br or Cl, provided that prior to cyclization, compounds wherein R$^5$ or R$^6$ is hydrogen are reacted with a suitable N-protecting group.

2. The process of claim 1 wherein R$^5$ is phenyl and R$^6$ is hydrogen.

3. The process of claim 1 wherein the palladium catalyst is PdX$_2$/ligand; Pd(PPh$_3$)$_4$; (R$^{11}$)$_3$P/ Pd$_2$(dba)$_3$; or Pd/C, wherein X is OAc or Cl, ligand is P(R$^{11}$)$_3$, dipyridyl, 2-aminopyridine, 2-cyano-pyridine, 2-dimethylaminopyridine, 1,10-phenanthroline, 2-methoxypyridine or (S)-(–)-nicotine, and wherein Ac is acetyl, R$^{11}$ is C$_1$ to C$^6$ alkyl or aryl, Ph is phenyl, and dba is dibenzylidene acetone.

4. The process of claim 1 wherein R$^8$MgL is isopropyl-magnesium chloride, 2-mesitylmagnesium bromide, o-tolylmagnesium bromide, 2-methoxyphenylmagnesium bromide, 2-methoxy-5-methylphenyl-magnesium bromide or N-methyl-piperidylmagnesium bromide, and R$^8$Li is n-butyllithium, sec-butyllithium, tert-butyllithium, methyllithium or phenyllithium.

5. The process of claim 1 wherein R$^5$ is phenyl, R$^6$ is hydrogen, the palladium catalyst is Pd(OAc)$_2$/dipyridyl, Pd(OAc)$_2$/P(R$^{11}$)$_3$ or PdCl$_2$/(PPh$_3$)$_2$, wherein Ac is acetyl, Ph is phenyl and R$^{11}$ is C$_1$ to C$^6$ alkyl or aryl, R$^8$MgL is isopropyl-magnesium chloride, 2-mesitylmagnesium bromide, o-tolylmagnesium bromide, 2-methoxyphenylmagnesium bromide, 2-methoxy-5-methyl-phenyl-magnesium bromide, 2,5-dimethoxyphenyl-magnesium bromide or N-methyl-piperidyl-magnesium bromide, and R$^8$Li is n-butyllithium, sec-butyllithium, tert-butyllithium, methyllithium or phenyllithium.

6. A process of claim 1 for preparing a compound of the formula

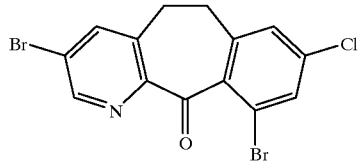

comprising:

(a) reacting a compound of the formula

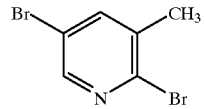

(i) with an amine of the formula NHR$^5$R$^6$, wherein R$^5$ is hydrogen and R$^6$ is C$_1$–C$_6$ alkyl, aryl or heteroaryl; R$^5$ is C$_1$–C$_6$ alkyl, aryl or heteroaryl and R$^6$ is hydrogen; R$^5$ and R$^6$ are independently selected from the group consisting of C$_1$–C$_6$ alkyl and aryl; or R$^5$ and R$^6$, together with the nitrogen to which they are attached, form a ring comprising 4 to 6 carbon atoms or comprising 3 to 5 carbon atoms and one hetero moiety selected from the group consisting of —O— and —NR$^9$—, wherein R$^9$ is H, C$_1$–C$_6$ alkyl or phenyl; in the presence of a palladium catalyst and carbon monoxide to obtain an amide of the formula:

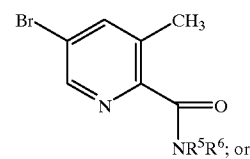

(ii) with an alcohol of the formula R$^{10}$OH, wherein R$^{10}$ is C$_1$–C$_6$ lower alkyl or C$_3$–C$_6$ cycloalkyl, in the presence of a palladium catalyst and carbon monoxide to obtain the ester of the formula

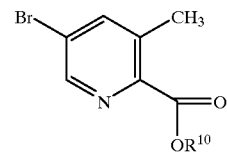

followed by reacting the ester with an amine of formula NHR$^5$R$^6$ to obtain the amide of step (i);

(b) reacting the amide of step (a) with an iodo-substituted compound of the formula

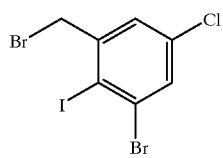

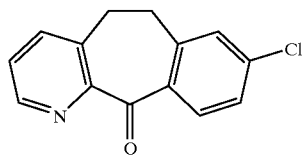

in the presence of a strong base to obtain a compound of the formula

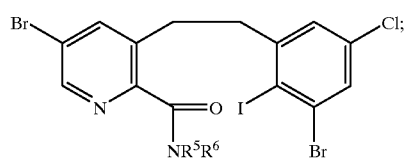

(c) cyclizing a compound of step (b) with a reagent of the formula R⁸MgL, wherein R⁸ is $C_1$–$C_8$ alkyl, aryl or heteroaryl and L is Br or Cl, provided that prior to cyclization, compounds wherein $R^5$ or $R^6$ is hydrogen are reacted with a suitable N-protecting group.

7. The process of claim 6 wherein $R^5$ is phenyl and $R^6$ is hydrogen.

8. The process of claim 6 wherein the palladium catalyst is PdX₂/ligand; Pd(PPh₃)₄; (R¹¹)₃P/ Pd₂(dba)₃; or Pd/C, wherein X is OAc or Cl, ligand is P(R¹¹)₃, dipyridyl, 2-aminopyridine, 2-cyano-pyridine, 2-dimethylaminopyridine, 1,10-phenanthroline, 2-methoxy-pyridine or (S)-(–)-nicotine, and wherein Ac is acetyl, R¹¹ is $C_1$ to $C_6$ alkyl or aryl, Ph is phenyl, and dba is dibenzylidene acetone.

9. The process of claim 6 wherein R⁸MgL is isopropyl-magnesium chloride, 2-mesitylmagnesium bromide, o-tolylmagnesium bromide, 2-methoxy-phenylmagnesium bromide, 2-methoxy-5-methylphenyl-magnesium bromide, 2,5-dimethoxyphenylmagnesium bromide or N-methyl-piperidylmagnesium bromide.

10. The process of claim 6 wherein $R^5$ is phenyl, $R^6$ is hydrogen, the palladium catalyst is Pd(OAc)₂/dipyridyl or Pd(OAc)₂/P(R¹¹)₃, wherein Ac is acetyl and R¹¹ is $C_1$ to $C_6$ alkyl or aryl, and R⁸MgL is isopropyl-magnesium chloride, 2-mesityl-magnesium bromide, o-tolyl-magnesium bromide, 2-methoxyphenyl-magnesium bromide, 2-methoxy-5-methyl-phenyl-magnesium bromide, 2,5-dimethoxyphenyl-magnesium bromide or N-methyl-piperidyl-magnesium bromide.

11. A process of claim 10 wherein $R^5$ is phenyl, $R^6$ is hydrogen, the palladium catalyst is Pd(OAc)₂/dipyridyl and R⁸MgL is 2-methoxy-phenyl-magnesium bromide.

12. A process of claim 11 wherein $R^6$ is reacted with a protecting group after step (a).

13. A process of claim 11 wherein $R^6$ is reacted with a protecting group after step (b).

14. A process of claim 1 for preparing a compound of the formula comprising:

(a) reacting a compound of the formula

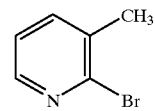

(i) with an amine of the formula NHR⁵R⁶, wherein $R^5$ is hydrogen and $R^6$ is $C_1$–$C_6$ alkyl, aryl or heteroaryl; $R^5$ is $C_1$–$C_6$ alkyl, aryl or heteroaryl and $R^6$ is hydrogen; $R^5$ and $R^6$ are independently selected from the group consisting of $C_1$–$C_6$ alkyl and aryl; or $R^5$ and $R^6$, together with the nitrogen to which they are attached, form a ring comprising 4 to 6 carbon atoms or comprising 3 to 5 carbon atoms and one hetero moiety selected from the group consisting of —O— and —NR⁹—, wherein $R^9$ is H, $C_1$–$C_6$ alkyl or phenyl; in the presence of a palladium catalyst and carbon monoxide to obtain an amide of the formula:

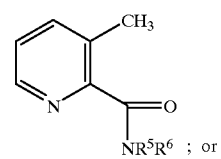 ; or (ii) with an alcohol of the formula R¹⁰OH, wherein $R^{10}$ is $C_1$–$C_6$ lower alkyl or $C_3$–$C_6$ cycloalkyl, in the presence of a palladium catalyst and carbon monoxide to obtain the ester of the formula

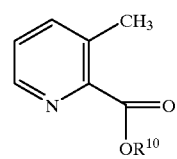

followed by reacting the ester with an amine of formula NHR⁵R⁶ to obtain the amide of step (i);

(b) reacting the amide of step (a) with an iodo-substituted compound of the formula

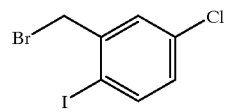

in the presence of a strong base to obtain a compound of the formula

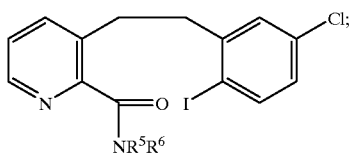

(c) cyclizing a compound of step (b) with a reagent of the formula $R^8MgL$ or $R^8Li$, wherein $R^8$ is $C_1$–$C_8$ alkyl, aryl or heteroaryl and L is Br or Cl, provided that prior to cyclization, compounds wherein $R^5$ or $R^6$ is hydrogen are reacted with a suitable N-protecting group.

15. The process of claim 14 wherein $R^5$ is phenyl and $R^6$ is hydrogen.

16. The process of claim 14 wherein the palladium catalyst is $PdX_2$/ligand; $Pd(PPh_3)_4$; $(R^{11})_3P/\ Pd_2(dba)_3$; or Pd/C, wherein X is OAc or Cl, ligand is $P(R^{11})_3$, dipyridyl, 2-aminopyridine, 2-cyano-pyridine, 2-dimethylaminopyridine, 1,10-phenanthroline, 2-methoxy-pyridine or (S)-(–)-nicotine, and wherein Ac is acetyl, $R^{11}$ is $C_1$ to $C_6$ alkyl or aryl, Ph is phenyl, and dba is dibenzylidene acetone.

17. The process of claim 14 wherein $R^8MgL$ is isopropylmagnesium chloride, 2-mesitylmagnesium bromide, o-tolylmagnesium bromide, 2-methoxy-phenylmagnesium bromide, 2-methoxy-5-methylphenyl-magnesium bromide, 2,5-dimethoxyphenylmagnesium bromide or N-methyl-piperidylmagnesium bromide and $R^8Li$ is n-butyllithium, sec-butyllithium, tert-butyllithium, methyllithium or phenyllithium.

18. The process of claim 14 wherein $R^5$ is phenyl, $R^6$ is hydrogen, the palladium catalyst is $Pd(OAc)_2$/dipyridyl, $Pd(OAc)_2/P(R^{11})_3$ or $PdCl_2/(PPh_3)_2$, wherein Ac is acetyl, Ph is phenyl, $R^{11}$ is $C_1$ to $C_6$ alkyl or aryl, $R^8MgL$ is isopropyl-magnesium chloride, 2-mesityl-magnesium bromide, o-tolyl-magnesium bromide, 2-methoxyphenyl-magnesium bromide, 2-methoxy-5-methyl-phenyl-magnesium bromide, 2,5-dimethoxyphenyl-magnesium bromide or N-methyl-piperidyl-magnesium bromide and $R^8Li$ is n-butyllithium, sec-butyllithium, tert-butyllithium, methyllithium or phenyllithium.

19. A process of claim 18 wherein $R^5$ is phenyl, $R^6$ is hydrogen, the palladium catalyst is $(PPh_3)_2PdCl_2$ and $R^8MgL$ is 2-methoxyphenyl-magnesium bromide or $R^8Li$ is n-butyllithium.

20. A process of claim 18 wherein $R^6$ is reacted with a protecting group after step (a).

21. A process of claim 18 wherein $R^6$ is reacted with a protecting group after step (b).

22. A process for preparing a compound of the formula 5

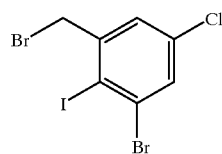

comprising:

i) brominating 2-amino chlorobenzoic acid of formula 6

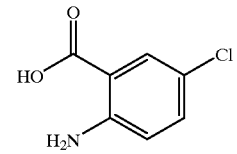

to obtain 2-amino-3-bromo-5-chlorobenzoic acid of formula 7

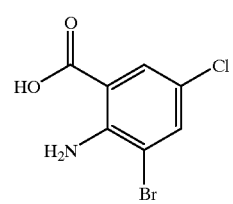

ii) iodonating the compound of formula 7 to obtain 2-iodo-3-bromo-5-chlorobenzoic acid of formula 8

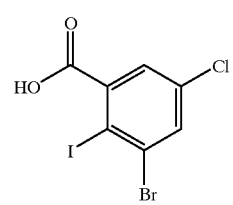

iii) reducing the carboxylic acid of the halo-substituted benzoic acid of formula 8 to obtain the corresponding hydroxy-methyl compound of formula 9

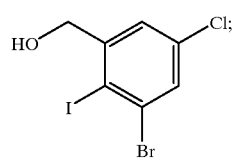

and iv) brominating the compound of formula 9.

23. A compound which is

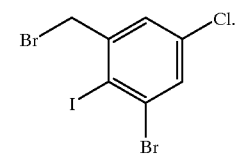

24. A process for preparing a compound of formula 5A

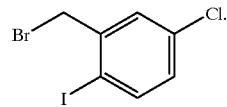

5A comprising:
i) iodonating the compound of formula 7A

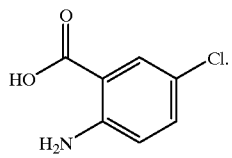

7A to obtain 2-iodo-5-chlorobenzoic acid of formula 8A

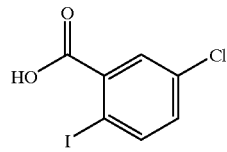

8A ii) reducing the carboxylic acid of the halo-substituted benzoic acid of formula 8A to obtain the corresponding hydroxy-methyl compound of formula 9A

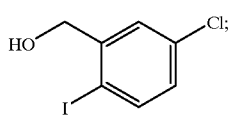

9A and
iii) brominating the compound of formula 9A.

25. A compound of the formula

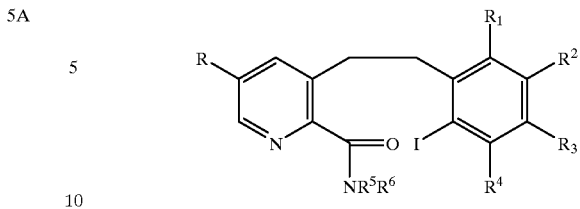

wherein R, $R^1$, $R^2$, $R^3$ and $R^4$ are independently selected from the group consisting of hydrogen and halo; and wherein $R^5$ is hydrogen and $R^6$ is $C_1$–$C_6$ alky, aryl or heteroaryl; $R^5$ is $C_1$–$C_6$ alkyl, aryl or heteroaryl and $R^6$ is hydrogen; $R^5$ and $R^6$ are independently selected from the group consisting of $C_1$–$C_6$ alkyl and aryl; or $R^5$ and $R^6$, together with the nitrogen to which they are attached, form a ring comprising 4 to 6 carbon atoms or comprising 3 to 5 carbon atoms and one hetero moiety selected from the group consisting of —O— and —$NR^9$—, wherein $R^9$ is H, $C_1$–$C_6$ alkyl or phenyl.

26. A compound of claim 25 selected from the group consisting of

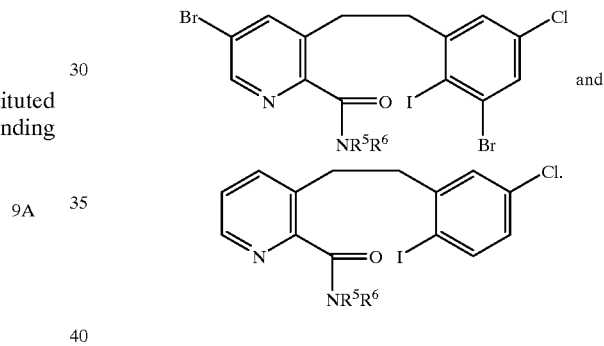

* * * * *